(12) United States Patent
Takase et al.

(10) Patent No.: US 7,182,971 B2
(45) Date of Patent: Feb. 27, 2007

(54) OIL COMPOSITION

(75) Inventors: Hideto Takase, Tokyo (JP); Shin Koike, Tokyo (JP); Hideaki Sakai, Tokyo (JP); Tsutomu Nishide, Tokyo (JP); Tadashi Hase, Tokyo (JP); Takatoshi Murase, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/488,251

(22) PCT Filed: Sep. 12, 2002

(86) PCT No.: PCT/JP02/09334

§ 371 (c)(1),
(2), (4) Date: Aug. 18, 2004

(87) PCT Pub. No.: WO03/024237

PCT Pub. Date: Mar. 27, 2003

(65) Prior Publication Data

US 2004/0265466 A1    Dec. 30, 2004

(30) Foreign Application Priority Data

Sep. 13, 2001   (JP)   ............... 2001-277669
Aug. 30, 2002   (JP)   ............... 2002-253927

(51) Int. Cl.
*A23D 7/005*     (2006.01)
(52) U.S. Cl. ...................... 426/601; 426/606
(58) Field of Classification Search .................... None
See application file for complete search history.

(56) References Cited

U.S. PATENT DOCUMENTS

| | | |
|---|---|---|
| 5,149,851 A | 9/1992 | Stout et al. |
| 5,151,291 A | 9/1992 | Tokairin et al. |
| 6,448,292 B2 * | 9/2002 | Koike et al. ................. 514/558 |
| 6,844,021 B2 * | 1/2005 | Koike et al. ................. 426/611 |
| 6,852,758 B2 * | 2/2005 | Koike et al. ................. 514/560 |

FOREIGN PATENT DOCUMENTS

| | | |
|---|---|---|
| EP | 1041136 | 10/2000 |
| JP | 0525915 | * 3/1989 |
| JP | 09013075 | 1/1997 |
| WO | 0110989 | 2/2001 |

OTHER PUBLICATIONS

U.S. Appl. No. 10/857,020 filed Jun. 1, 2004, Moriwaki, et al.
U.S. Appl. No. 10/761,358 filed Jan. 22, 2004, Koike, et al.

* cited by examiner

*Primary Examiner*—Carolyn Paden
(74) *Attorney, Agent, or Firm*—Oblon, Spivak, McClelland, Maier & Neustadt, P.C.

(57) ABSTRACT

Disclosed herein is an oil composition comprising the following components (A) and (B):(A) 15 to 70% by weight of diglycerides in which less than 15% by weight of the constitutive fatty acids are (3 type unsaturated fatty acids; and (B) 30 to 85% by weight of a triglyceride in which at least 15% by weight of the constitutive fatty acids are (3 type unsaturated fatty acids. The oil composition is good in flavor, hard to be colored, excellent in hydrolytic stability and resistance to oxidation, good in emulsion stability and excellent in intake balance among fatty acids even under severe conditions that heating is performed at a high temperature for a long period of time, can be widely developed to medicinal preparations and foods and moreover exhibit an excellent inhibitory effect on accumulation of body fat by ingestion of a small amount of diglycerides.

13 Claims, No Drawings

OIL COMPOSITION

BACKGROUND OF THE INVENTION

1. Field of the Invention

The present invention relates to an oil or fat (hereafter referred to as "oil" merely) composition which is good in flavor, hard to be colored and high in hydrolysis stability, oxidation stability and emulsion stability even under severe conditions that heating is performed at a high temperature for a long period of time and thus can be used in various kinds of pharmaceutical preparations, foods and feeds and moreover has an excellent inhibitory effect on accumulation of body fat.

2. Related Background Art

In recent years, researches on the relationship between distribution of body fat and various life-style related diseases have been advanced. In particular, it has been shown that the accumulation of visceral fats such as intraperitoneal fat and hepatic fat has high correlation with diabetes, hyperlipidemia, hepatic diseases, hypertension, etc., to say nothing of obesity. It is accordingly important from the viewpoint of preventing and treating these diseases to reduce the body fat.

Techniques of using diglycerides as edible oils have been already disclosed (Japanese Patent Application Laid-Open No. 7-16053, U.S. Pat. No. 4,656,045, EP 0525915 and WO 96/32022, etc.), and it has been found that diglycerides have an effect to reduce the accumulation of body fat to prevent obesity (Japanese Patent Application Laid-Open No. 4-300828 and U.S. Pat. No. 6,004,611, etc.). The diglycerides are considered to inhibit increase of neutral lipid in blood, thereby reducing the accumulation of body fat.

However, a diglyceride is hydrolyzed and oxidized by heating or storage for a long period of time like triglycerides. The smoke point of the diglyceride is lowered by the influence of a fatty acid liberated by the hydrolysis to cause problems on smell during cooking and operability. In addition, problems of production of odor by deterioration, coloring, deterioration of flavor, etc. are also caused by the oxidation.

There is no extremely useful prior art for a method for improving the hydrolytic stability of an oil (triglyceride). On the other hand, as techniques for preventing oxidation, there have been proposed a method of adding any of various kinds of antioxidant to an oil for frying and a method of adding citric acid as a synergist (Theory and Practice of Fried Food, edited by Saiwai Shobo, 1976). However, in the latter method in particular, citric acid or a salt thereof is hardly soluble in oils, and so its effect has not been sufficient (Japanese Patent Application Laid-Open No. 49-86557).

On the other hand, triglycerides, particularly, triglycerides containing ω3 type unsaturated fatty acid(s) have been known to have physiological effects, for example, an anti-allergic effect (Japanese Patent Application Laid-Open No. 63-36744) and an effect of preventing diseases of the circulatory system (Japanese Patent Application Laid-Open No. 61-85143). On the basis of such properties, application to foods and drinks for infants and patients of allergic diseases has been proposed (Japanese Patent Application Laid-Open No. 9-121766).

However, such highly unsaturated fatty acid-containing triglycerides are very easy to be oxidized. In Japanese Patent Application Laid-Open Nos. 4-46998 and 8-116878, etc., applications of these triglycerides to edible oils have been proposed. However, oxidation stability has not been sufficient. In order to solve such a problem, an addition of a great amount of an antioxidant has been known as a method for preventing the oxidation of triglycerides. However, antioxidants greatly soluble in a triglyceride are few, and there is a limit to use. In addition, the antioxidant effect of the few antioxidants is not sufficient even when they are used in a great amount. As another method for preventing the oxidation, powdering (Japanese Patent Application Laid-Open Nos. 9-121766 and 7-313057) or the like has been conducted. However, it has been difficult to widen a variation as a preparation. As described above, any technique for widely handling the triglycerides containing the highly unsaturated fatty acid(s) has not been yet established under the circumstances.

With respect to the oxidation stability of the highly unsaturated fatty acid-containing triglycerides and the diglycerides, there is a particularly strong demand for improvement in institutional or processing oils used under particularly severe conditions in fry works, daily dish shops, eating houses, restaurants, etc. Ascorbyl palmitate, tocopherol or the like may be used as an antioxidant in an increased amount in some cases. However, its effect is not sufficient. With respect to oils, there are problems of increase in smoke attendant on rise of acidic value, appearance discoloration and the like during cooking. With respect to fried products, there are problems of deterioration of flavor, color tone and/or appearance, and the like due to soap odor or the like based on decomposed fatty acids. More specifically, the diglycerides have a unique effect of inhibiting the accumulation of body fat and on one hand involve a problem that their uses are limited according to service conditions. On the other hand, in the highly unsaturated fatty acid-containing triglycerides, any solution to sole use at a high temperature has not been yet found from the viewpoints of oxidation stability and flavor. In addition, any technique for widely handling the highly unsaturated fatty acid-containing triglycerides has not be yet established due to great restrictions on preparations.

SUMMARY OF THE INVENTION

It is therefore an object of the present invention to provide an oil composition which is good in flavor, hard to be colored and excellent in hydrolysis stability, resistance to oxidation and emulsion stability even under severe conditions that heating is performed at a high temperature for a long period of time, can be widely developed to pharmaceutical preparations, foods and feeds and moreover has an excellent inhibitory effect on accumulation of body fat.

The present inventors have found that when the contents of diglycerides and a triglyceride in an oil composition and the contents of specific unsaturated fatty acids in fatty acids constituting such glycerides are varied, the amount of an antioxidant dissolved in the oil composition is increased, and the oil composition can be provided as an oil composition which is good in flavor, hard to be colored, excellent in hydrolysis stability and resistance to oxidation, good in emulsion stability and excellent in intake balance among fatty acids even under severe conditions that heating is performed at a high temperature for a long period of time, can be widely developed to pharmaceutical preparations and foods and moreover has an excellent inhibitory effect on accumulation of body fat, and also that this oil composition is excellent in the effect of inhibiting the accumulation of body fat even when the content of the diglycerides is lower than the conventional diglyceride-containing oil composition (U.S. Pat. No. 6,004,611).

According to the present invention, there is thus provided an oil composition comprising the following components (A) and (B):

(A) 15 to 70% by weight of diglycerides in which less than 15% by weight of the constitutive fatty acids are ω3 type unsaturated fatty acids; and (B) 30 to 85% by weight of a triglyceride in which at least 15% by weight of the constitutive fatty acids are ω3 type unsaturated fatty acids.

According to the present invention, there is also provided a food, feed or pharmaceutical comprising such an oil composition.

DETAILED DESCRIPTION OF THE PREFERRED EMBODIMENTS

The oil composition according to the present invention comprises 15 to 70% by weight (hereafter indicated merely by "%") of diglycerides as the component (A) in which less than 15% of the constitutive fatty acids are ω3 type unsaturated fatty acids. From the viewpoints of the stability, physiological effect and emulsion stability of the oil, the content of the diglycerides is preferably 20 to 59.9%, more preferably 30 to 49.9%, particularly preferably 35 to 49.9%. Although the diglycerides include 1,3-diglyceride and 1,2-diglyceride, the 1,3-diglyceride is preferred from the viewpoint of the physiological effect. It is desirable from the viewpoints of the physiological effect, stability of the oil and industrial productivity that the content of the 1,3-diglyceride in the oil composition be 9 to 55%, preferably 12 to 50%, more preferably 16 to 40%, particularly preferably 20 to 39%.

The term "ω3 type unsaturated fatty acid" as used herein means a fatty acid that a first carbon-carbon double bond is located on the third carbon atom from an ω position, and that has at least 2 carbon-carbon double bonds. Examples thereof include unsaturated fatty acids having 14 to 19 carbon atoms, such as α-linolenic acid and stearidonic acid and unsaturated fatty acids having 20 to 30 carbon atoms, such as eicosapentaenoic acid, docosapentaenoic acid and docosahexaenoic acid, with α-linolenic acid being particularly preferred. The ω3 type unsaturated fatty acids are desirably contained in a proportion of preferably 0 to 14.9%, more preferably 0.1 to 14%, still more preferably 0.5 to 12%, particularly preferably 1 to 10%, most preferably 4 to 10%, in the constitutive fatty acids of the diglycerides from the viewpoint of the stability and physiological effect of the oil.

It is preferred from the viewpoints of oxidation stability and intake balance among fatty acids that an ω9 type unsaturated fatty acid be contained as a residual constitutive fatty acid of the diglycerides in a proportion of 1 to 70%, preferably 5 to 60%, more preferably 10 to 50%, particularly preferably 20 to 45%. Examples of the ω9 type unsaturated fatty acid include unsaturated fatty acids having 10 to 24 carbon atoms, preferably 16 to 22 carbon atoms, such as oleic acid, eicosamonoenoic acid and docosamonoenoic acid, with oleic acid being particularly preferred. From the viewpoint of development of the physiological effect, the olein-olein diglyceride content is preferably lower than 45%, more preferably 0 to 40%.

It is preferred from the viewpoints of oxidation stability, intake balance among fatty acids and development of physiological activity effect derived from the ω3 type unsaturated fatty acids that an ω6 type unsaturated fatty acid having 18 to 22 carbon atoms, such as linoleic acid or γ-linolenic acid be contained as a further constitutive fatty acid of the diglycerides in a proportion of 2 to 80%, preferably 5 to 70%, more preferably 10 to 60%, particularly preferably 20 to 50%. It is desirable from the oxidation stability and development of physiological activity effect that a weight ratio of linoleic acid to oleic acid contained be 0.01 to 2.0, preferably 0.1 to 1.8, particularly 0.3 to 1.7.

It is preferred from the viewpoints of the development of physiological activity and industrial productivity that 55 to 100%, preferably 70 to 100%, more preferably 80 to 100, particularly preferably 90 to 100% of the constitutive fatty acids of the diglycerides be unsaturated fatty acids having 10 to 24 carbon atoms, particularly preferably unsaturated fatty acids having 16 to 22 carbon atoms. The residual constitutive saturated fatty acids preferably have 14 to 24 carbon atoms, preferably 16 to 22 carbon atoms.

The diglycerides can be obtained by an optional process such as transesterification of an oil with glycerol or esterification of a fatty acid derived from an oil with glycerol. The reaction method thereof may be either a chemical reaction method making use of an alkali catalyst or the like or a biochemical reaction method making use of a lipolytic enzyme such as lipase.

Examples of the oil include vegetable oils such as soybean oil, rapeseed oil, palm oil, rice oil, corn oil, sunflower oil, safflower oil, olive oil and sesame oil; animal oils such as beef tallow, lard and fish oil; and hardened oils, fractionated oils, transesterified oils and random transesterified oils thereof.

The oil composition according to the present invention comprises 30 to 85% of a triglyceride as the component (B) in which at least 15% of the constitutive fatty acids are ω3 type unsaturated fatty acids. It is desirable from the viewpoints of the stability, physiological effect and emulsion stability of the oil that the content of the triglyceride be preferably 40 to 79.9%, particularly 50 to 69.9%. Examples of the ω3 type unsaturated fatty acids include unsaturated fatty acids having 14 to 19 carbon atoms, such as α-linolenic acid and stearidonic acid and unsaturated fatty acids having 20 to 30 carbon atoms, such as eicosapentaenoic acid, docosapentaenoic acid and docosahexaenoic acid, with α-linolenic acid being particularly preferred. The ω3 type unsaturated fatty acids are desirably contained in a proportion of 15 to 90%, preferably 17 to 60%, more preferably 17 to 40%, particularly preferably 20 to 30% in the constitutive fatty acids of the triglyceride from the viewpoint of the stability and physiological effect of the oil. The content of α-linolenic acid in the ω3 type unsaturated fatty acids is preferably at least 50%, more preferably 70 to 100%, particularly preferably 90 to 100%.

It is desirable from the viewpoints of oxidation stability and intake balance among fatty acids that an ω9 type unsaturated fatty acid be contained as a residual constitutive fatty acid of the triglyceride in a proportion of 1 to 80%, preferably 5 to 70%, more preferably 10 to 60%, particularly preferably 20 to 50%. Examples of the ω9 type unsaturated fatty acid include unsaturated fatty acids having 10 to 24 carbon atoms, preferably 16 to 22 carbon atoms, such as oleic acid, eicosamonoenoic acid and docosamonoenoic acid, with oleic acid being particularly preferred.

It is preferred from the viewpoints of intake balance among fatty acids and development of physiological activity effect derived from the ω3 type unsaturated fatty acids that an ω6 type unsaturated fatty acid having 18 to 22 carbon atoms, such as linoleic acid or γ-linolenic acid be contained as a further constitutive fatty acid of the triglyceride in a proportion of 1 to 60%, preferably 2 to 50%, more preferably 5 to 40%, particularly preferably 10 to 30%.

It is preferred from the viewpoints of the development of physiological activity that 40 to 100%, preferably 55 to 100%, more preferably 70 to 100, particularly preferably 80 to 100% of the constitutive fatty acids of the triglyceride be unsaturated fatty acids having 12 to 24 carbon atoms, preferably unsaturated fatty acids having 16 to 22 carbon atoms. The residual constitutive saturated fatty acids preferably have 14 to 24 carbon atoms, preferably 16 to 22 carbon atoms.

As such a triglyceride, may be used an oil such as perilla oil, linseed oil, wax tree kernel oil or fish oil, and it is prepared by esterification of a ω3 type unsaturated fatty acid such as α-linolenic acid with glycerol, or the like. The reaction method thereof may be either a chemical reaction method making use of an alkali catalyst or the like or a biochemical reaction method making use of a lipolytic enzyme such as lipase.

The constitutive fatty acids in the triglyceride can be prepared by mixing or transefterifying the above-described oil containing the ω3 type unsaturated fatty acids as constitutive unsaturated fatty acids with another oil such as rapeseed oil, soybean oil, sunflower oil, safflower oil, olive oil, sesame oil, corn oil or cotton-seed oil. The triglyceride used herein may be liquid or solid at normal temperature.

The residual components of the oil composition according to the present invention are a monoglyceride, free fatty acids and the like. The monoglyceride is desirably contained in a proportion of 0 to 10%, preferably 0.1 to 10%, more preferably 0.1 to 5%, still more preferably 0.1 to 1.5%, particularly preferably 0.1 to 1% in the oil composition from the viewpoints of prevention of smoking upon heating, flavor, industrial productivity, emulsification, etc. The content of the free fatty acids (salts) is preferably reduced to at most 3.5%, more preferably 0 to 2.5%, still more preferably 0 to 1.5%, particularly preferably 0 to 1%, most preferably 0 to 0.5% from the viewpoints of prevention of smoking upon heating and flavor.

The content of fatty acids having at least 4 carbon-carbon double bonds in all the constitutive fatty acids in the oil composition according to the present invention is preferably 0 to 40%, more preferably 0 to 20%, still more preferably 0 to 10%, particularly preferably 0 to 1% from the viewpoints of physiological effect, oxidation stability, coloring, etc., and such fatty acids are most preferably substantially not contained.

An antioxidant is preferably added in a proportion of 0.004 to 5%, more preferably 0.004 to 2%, particularly preferably 0.02 to 1% to the oil composition according to the present invention from the viewpoints of oxidation stability, coloring, etc. Any antioxidant may be added so far as it is commonly used in foods, pharmaceuticals and feeds. However, a natural antioxidant, phospholipid, catechin, BHT (dibutylhydroxytoluene), BHA (butylhydroxyanisole), TBHQ (tert-butylhydroquinone), propyl gallate, L-proline, rosemary extract, vitamin C or a derivative thereof, or vitamin E is preferred from the viewpoint of antioxidant property. Two or more of these antioxidants may be used in combination. For example, rosemary extract and vitamin C or a derivative thereof, or vitamin C or a derivative thereof and vitamin E are preferably contained in combination. Rosemary extract, vitamin C or a derivative thereof and vitamin E are particularly preferably contained in combination.

The rosemary extract is an extract products by drying and grinding leaves of rosemary which is a plant of Lamiaceae, and extracting them with water, hot water, hexane, ethanol, acetone, ethyl acetate or a mixed solvent thereof. In the present invention, besides the above-described extracts with the organic solvent, oleo-resin preparations prepared from this extract, or preparations of rosemanol, calsonol, isorosmarol, etc. which are constituents thereof may also be used. Products (hereinafter referred to as deodorized products) obtained by subjecting these extracts to a deodorizing treatment by a method under reduced pressure, a method under heating and reduced pressure, a supercritical extraction method, a column adsorption method or the like are particularly preferred from the viewpoint of flavor. The amount of a solvent remaining in these deodorized products is preferably at most 20 ppm, particularly preferably at most 15 ppm. Examples of commercially available rosemary extracts include Herbalox Type O, Herbalox Type HT-O, Herbalox Type 25, Duolite NMH and Duolite NM-1 (all, products of Kalsec Co.), and Leomi-ru E and Leomi-ru IO (both, product of Lion Corporation).

The content of these rosemary extracts in the oil composition according to the present invention is preferably 0.02 to 0.5%, more preferably 0.05 to 0.35%, particularly preferably 0.1 to 0.3% in terms of dewatered and desolvated products from the viewpoint of imparting good antioxidant property to the oil composition.

Examples of vitamin C or the derivative thereof include L-ascorbic acid fatty acid esters.

The L-ascorbic acid fatty acid esters are preferably those dissolved in the diglyceride-containing oil composition, more preferably higher fatty acid esters the number of carbon atoms of the acyl group in which is 12 to 22, particularly preferably L-ascorbyl palmitate or L-ascorbyl stearate, most preferably L-ascorbyl palmitate.

The content of vitamin C or the derivative thereof in the oil composition according to the present invention is preferably at least 0.004%, more preferably 0.006 to 0.08%, particularly preferably 0.008 to 0.06% in terms of ascorbic acid from the viewpoint of imparting good antioxidant property to the oil composition.

As vitamin E, is used α-, β-, γ- or δ-tocopherol or a mixture thereof, with δ-tocopherol being particularly preferred from heat resistance. Examples of commercially available vitamin E products include E Mix D and E Mix 80 (both, products of Eisai Co., Ltd.), MDE-6000 (product of Yashiro Co., Ltd.), and E Oil-400 (product of Riken Vitamin Co., Ltd.).

The content of vitamin E in the oil composition according to the present invention is preferably at least 0.01%, more preferably 0.02 to 0.4%, particularly preferably 0.05 to 0.3% in terms of tocopherol from the viewpoint of imparting good antioxidant property to the oil composition.

When an organic carboxylic acid having 2 to 8 carbon atoms, such as a hydroxycarboxylic acid, dicarboxylic acid or tricarboxylic acid, or a salt thereof is contained in the oil composition according to the present invention, hydrolysis is more inhibited. It is hence preferable to contain such a compound. Specific preferable examples thereof include citric acid, succinic acid, maleic acid, oxalic acid, aconitic acid, itaconic acid, citraconic acid, tartaric acid, fumaric acid and malic acid. Citric acid, tartaric acid and malic acid are more preferred. Examples of commercially available citric acid products include citric acid (crystal) monoglyceride (product of ADM Co.) and purified citric acid crystal monoglyceride (product of Fuso Chemical Industries Co., Ltd.). Examples of salts of the organic carboxylic acids include alkali metal salts and alkaline earth metal salts thereof, with the sodium salts and calcium salts being preferred.

As the organic carboxylic acid, may be used an extract or crude drug containing the organic carboxylic acid. The extract or crude drug may be used as a product in the form of powder, concentrate or the like, which is prepared by extracting fruits of lemon, citron, Japanese apricot and commercially available.

The content of the organic carboxylic acid or the salt thereof in the oil composition according to the present invention is at least 0.001%, preferably 0.001 to 0.2%, more preferably 0.0015 to 0.15%, particularly preferably 0.002 to 0.1% from the viewpoint of the effect of inhibiting hydrolysis. When the extract or crude drug is used, it is only necessary to add it in such a manner that the amount of the organic carboxylic acid contained in the extract or crude drug falls within the above range.

It is preferred from the viewpoint of antifoaming property that a silicone be further contained in the oil composition according to the present invention in addition to the antioxidant.

Examples of the silicone include preparations (KS-66, KS-69, KF-96, KM-72, etc., all products of Shin-Etsu Chemical Co., Ltd.; THF450, TSA737, etc., all products of Toshiba Silicone Co., Ltd.) known as antifoaming agents for food, such as dimethyl polysiloxane. The oxidation stability of the oil composition according to the present invention is still more improved by containing the silicone in the composition, and the deterioration of flavor upon use of the oil composition is also improved.

The content of the silicone in the oil composition according to the present invention is preferably at least 0.3 ppm, more preferably 0.5 to 10 ppm, particularly preferably 1 to 10 ppm.

The oil composition according to the present invention can be obtained by optionally adding the organic carboxylic acid, the rosemary extract, vitamin C or the derivative thereof, vitamin E, the silicone, etc. to the diglyceride-containing oil of the above-described composition and suitably heating and stirring the resultant mixture. The rosemary extract, vitamin C derivative, vitamin E and the like may also be dissolved in a solvent such as ethanol in advance before the addition thereof.

The oil composition according to the present invention is stable to long-time heating and storage and useful as, for example, an edible oil. The oil composition according to the present invention is also useful as an antioxidant that can improve the oxidation stability of an ordinary edible oil by adding it to the edible oil.

The oil composition according to the present invention preferably further comprises phytosterol. The phytosterol is a component having a cholesterol-reducing effect. The content of the phytosterol in the oil composition according to the present invention is preferably at least 0.05%, particularly at least 0.3%. The content of phytosterol in a commonly sold oil composition prepared using, as a raw material, a fatty acid obtained by distillation is reduced. In such a case, the phytosterol may preferably be added in such a manner that the content thereof amounts to at least 0.05%, and preferably falls within a range of 0.05 to 1.2%. When it is intended to reduce cholesterol to a greater extent than ordinary plant oils, the phytosterol may also be added in an amount of 1.2 to 20%, preferably 1.2 to 4.5%. Examples of the phytosterol used in the present invention include free substances such as α-sitosterol, β-sitosterol, stigmasterol, campesterol, α-sitostanol, β-sitostanol, stigmastanol, campestanol and cycloartenol, and besides esters thereof, such as fatty acid esters, ferulic acid esters and cinnamic acid esters.

The oil composition according to the present invention preferably further comprises a crystallization inhibitor.

Examples of crystallization inhibitors used in the present invention include polyol fatty acid esters such as polyglycerol condensed ricinoleic acid esters, polyglycerol fatty acid esters, sucrose fatty acid esters, sorbitan fatty acid esters, polyoxyethylene sorbitan fatty acid esters and propylene glycol fatty acid esters.

Among these polyol fatty acid esters, polyglycerol fatty acid esters, sucrose fatty acid esters, sorbitan fatty acid esters whose HLB (Griffin's equation, J. Soc. Cosmet. Chem., 1, 311 (1949)) is at most 4, particularly at most 3 are preferred.

The crystallization inhibitor is preferably contained in a proportion of 0.02 to 2%, preferably 0.02 to 0.5%, particularly preferably 0.05 to 0.2% in the oil composition according to the present invention from the viewpoint of improving stability at a low temperature.

The oil composition according to the present invention has excellent physiological activities such as effects of inhibiting accumulation of body fat, inhibiting increase of serum triglycerides, inhibiting increase of chylomicron triglycerides, inhibiting accumulation of visceral fats, inhibiting increase of body weight, inhibiting rise of blood sugar and improving insulin resistance. In addition, since it is good in flavor, hard to be colored and high in hydrolytic stability and the like even under severe conditions that heating is performed at a high temperature for a long period of time, and thus excellent in suitability for frying, its uses are not limited. Since the oil composition according to the present invention has such excellent properties, it can be used in foods, feeds and pharmaceuticals in the form of an oil-in-water type emulsion, water-in-oil type emulsion, capsule, tablet, granule, powder, gel, pellet, oil or the like.

With respect to the foods, the oil composition can be used as processed oil foods containing the oil composition as a part of food. Examples of such processed oil-containing foods include healthy foods, functional foods and specified healthy foods that the specified functions are exhibited to promote health. Examples of specific products thereof include bakery foods such as bread, cakes, biscuits, pies, pizza crusts and bakery mixes; oil-in-water type emulsions such as soup, sauce, dressings, mayonnaises, coffee whiteners, ice creams and whipped creams; water-in-oil type emulsions such as margarine, margarine-like spreads and butter creams; snack confectionery such as potato chips; confectionery such as chocolate, caramels, candies and desserts; processed meat products such as ham, sausage and Hamburg steak; dairy products such as milk, cheese and yogurt; and frying shortening, baking shortening, dough, enrober oils, filling oils, noodles, frozen foods, retort foods, drinks and roux. Such processed oil food can be produced by adding food materials commonly used according to the kind of the processed oil food in addition to the oil composition. It is preferred that the amount of the oil composition according to the present invention to be incorporated in food be generally 0.1 to 100%, particularly 1 to 80% though it varies according to the kind of the food. It may also be used as a food material of a cooking oil or the like used for fried food or frizzled food. In particular, it is suitable for use in cooking daily dish such as croquette, tempura, pork cutlet, food fried without coat, fried fishes and harumaki (spring roll); snack confectionery such as potato chips, tortilla chips and fabricated potato; fried confectionery such as fried Japanese cracker (age senbei); and fried potato, fried chicken, doughnut and instant noodle.

When an oil derived from a food material is contained because of necessity for preparation of a product, a Weight ratio of the oil derived from the food material to the oil composition according to the present invention is preferably 95:5 to 1:99, more preferably 95:5 to 5:95, still more preferably 85:15 to 5:95, particularly preferably 40:60 to 5:95.

The oil composition according to the present invention can be used in a pharmaceutical. Examples of the pharmaceuticals include oral preparations such as solid preparations, liquid preparations and gel preparations. Such an oral preparation can be prepared by adding an excipient, a disintegrator, a binder, a lubricant, a surfactant, an alcohol, water, a water-soluble polymer, an edulcorant, a taste corrigent, an acid corrigent and/or the like commonly used according to the form of the oral preparation in addition to the oil composition. It is preferred that the amount of the oil composition according to the present invention to be incorporated in the oral preparation be generally 0.1 to 80%, particularly 0.2 to 50% though it varies according to the application and form of the medicine. With respect to the dose of the oil composition as a medicament, it is-preferably administered in a dose of 0.2 to 50 g per day. Meanwhile, the administration may be once per day, or may be divided into several times per day.

The oil composition according to the present invention can be used in a feed. Examples of the feeds include feeds for livestock used in cattle, swine, fowl, sheep, horseflesh, etc., feeds for small animals used in rabbit, rats, mice, etc., feeds for fishes and shellfishes used in eels, sea breams, young yellowtails, lobsters, etc., and pet foods used in dogs, cats, small birds, squirrels, etc. It is preferred that the amount of the oil composition according to the present invention to be incorporated in the feed be generally 1 to 30%, particularly 1 to 20% though it varies according to the application of the feed. The oil composition according to the present invention may be used by replacing the whole or a part of an oil in a feed by it.

The feed can be produced by mixing feed materials commonly used, such as meat, proteins, cereals, brans, meals, saccharides, vegetables, vitamins and minerals, with the oil composition. Examples of the meat include meat or game of cattle, swine, sheep (mutton or ram), rabbit, kangaroo, etc., and by-products and processed products thereof; rendering products of the above-mentioned raw materials, such as meatball, meat-bone meal and chicken meal; and fish and fish meal of tuna, bonito, bluefish, sardine, scallop, turbo, etc. Examples of the proteins include milk proteins such as casein whey, and plant proteins such as soybean protein, the cereals include wheat, barley, rye, milo and corn. Examples of the brans include rice bran and wheat bran. Examples of the meals include soybean meal. The total amount of the meat, proteins, cereals, brans and meals in the feed is preferably 5 to 95%. Examples of the saccharides include glucose, oligosaccharides, sugar, molasses, starch and syrup, and the they are preferably contained in an amount of 5 to 80% in the feed. Examples of the vegetables include vegetable extracts, and the they are preferably contained in an amount of 1 to 30% in the feed. Examples of the vitamins include vitamin A, B1, B2, D and E, niacin, pantothenic acid and carotene, and the they are preferably contained in an amount of 0.05 to 10% in the feed. Examples of the minerals include calcium, phosphorus, sodium, potassium, iron, magnesium and zinc, and the they are preferably contained in an amount of 0.05 to 10% in the feed. Besides the above, a gelling agent, a shape-retaining agent, a pH adjustor, a seasoning, a preservative, a nutritional supplement and the like which are commonly used in feed may also be contained.

The oil composition according to the present invention can be used in an oil-in-water type emulsion. A weight ratio of an oil phase to a water phase is 1/99 to 90/10, preferably 10/90 to 80/20, particularly preferably 30/70 to 75/25. An emulsifier is preferably contained in an amount of 0.01 to 5%, particularly 0.05 to 3%. Examples of the emulsifier include various kinds of proteins such as egg proteins, soybean proteins, milk proteins, proteins separated from these proteins and (partially) decomposed products of these proteins, sucrose fatty acid esters, sorbitan fatty acid esters, polyoxyethylene sorbitan fatty acid esters, glycerol fatty acid monoesters, polyglycerol fatty acid esters, polyglycerol condensed ricinoleic acid esters, glycerol organic acid fatty acid esters, propylene glycol fatty acid esters, lecithin and enzymatically decomposed lecithin. A stabilizer is preferably contained in an amount of 0 to 5%, particularly 0.01 to 2%. Examples of the stabilizer include thickening polysaccharides such as xanthan gum, gellan gum, guar gum, carrageenan, pectin, tragacanth gum and konjak mannan, and starch. A phytosterol is preferably contained in an amount of 0 to 10%, more preferably 1 to 7%, particularly preferably 2 to 5%. In addition, flavorings such as common salt, saccharides, vinegar, fruit juices and seasoning, spicery such as spices and flavors, a colorant, a preservative, an antioxidant, etc. may be used. These raw materials may be used to prepare oil-in-water type oil-containing foods such as mayonnaises, dressings, coffee whiteners, ice creams, whipped creams and drinks in accordance with a method known per se in the art.

The oil composition according to the present invention can be used in a water-in-oil type emulsion. A weight ratio of a water phase to an oil phase is 85/15 to 1/99, preferably 80/20 to 10/90, particularly preferably 70/30 to 35/65. An emulsifier is preferably contained in an amount of 0.01 to 5%, particularly 0.05 to 3%. Examples of the emulsifier include various kinds of proteins such as egg proteins, soybean proteins, milk proteins, proteins separated from these proteins and (partially) decomposed products of these proteins, sucrose fatty acid esters, sorbitan fatty acid esters, polyoxyethylene sorbitan fatty acid esters, glycerol fatty acid monoesters, polyglycerol fatty acid esters, polyglycerol condensed ricinoleic acid esters, glycerol organic acid fatty acid esters, propylene glycol fatty acid esters, lecithin and enzymatically decomposed lecithin. A phytosterol is preferably contained in an amount of 0 to 10%, more preferably 1 to 7%, particularly preferably 2 to 5%. In addition, flavorings such as common salt, saccharides, vinegar, fruit juices and seasoning, spicery such as spices and flavors, a stabilizer such as a thickening polysaccharide or starch, a colorant, a preservative, an antioxidant, etc. may be used. These raw materials may be used to prepare water-in-oil type oil-containing foods such as margarine, margarine-like spreads and butter creams in accordance with a method known per se in the art.

The oil composition according to the present invention can be used in portable oil-containing foods. The oil content in such a food is preferably 1 to 30%, particularly preferably 1 to 20%. A phytosterol is preferably contained in an amount of 0 to 20%, more preferably 1 to 20%, particulary preferably 2 to 15%. A saccharide such as sucrose, glucose, fructose, maltose, xylitol, sorbitol, erythritol or starch is preferably contained in an amount of 40 to 99%. A carbonate foaming agent composed of an expanding agent such as sodium hydrogencarbonate and an acid agent such as tartaric acid, fumaric acid or citric acid is preferably contained in an amount of 0 to 20%, particularly preferably 1 to 10%. These raw materials may be used to prepare portable oil-containing foods such as tablet confectionery, candy, caramel and gummy in accordance with a method known per se in the art. In particular, the ability to dissolve in a mouth is improved by the use of the carbonate foaming agent.

The oil composition according to the present invention can be used in bakery foods. The oil content in such a food is preferably 1 to 40%, particularly preferably 5 to 35%. The content of a phytosterol is preferably 0 to 20%, more preferably 1 to 20%, particularly preferably 1 to 15%. The content of wheat flour is preferably 10 to 70%, particularly preferably 20 to 60%. At least one of the whole egg, yolk, albumen, separated products thereof and decomposed products thereof is preferably contained in an amount of 0 to 30%, particularly preferably 5 to 25%. Common salt is preferably contained in an amount of 0 to 2%, particularly preferably 0.1 to 1%. A saccharide and baking powder are is preferably contained in amounts of 0 to 2.5% and 0 to 1%, respectively. These raw materials may be used to prepare bakery foods such as bread, cakes and cookies in accordance with a method known per se in the art.

Having generally described this invention, a further understanding can be obtained by reference to certain specific examples which are provided herein for purposes of illustration only and are not intended to be limiting unless otherwise specified.

EXAMPLES

Example 1

The following oil compositions were prepared.

Diglyceride Oil A:

Soybean oil fatty acid (650 parts by weight) and glycerol (107 parts by weight) were subjected to esterification at 40° C. for 5 hours under 0.07 hPa using Lipozyme IM (product of Novo Nordisk Industry Co.). The enzyme was then separated by filtration, and the resultant filtrate was subjected to molecular distillation at 235° C. The distillate thus obtained was washed with water and then deodorized at 235° C. for 1 hour to obtain Diglyceride Oil A.

Diglyceride Oil B:

After a mixture of soybean oil fatty acid (455 parts by weight), the content of saturated fatty acids in which had been reduced by winterization, rapeseed oil fatty acid (195 parts by weight) and glycerol (107 parts by weight) were subjected to esterification in the same manner as in Diglyceride Oil A. The enzyme was then separated by filtration, and the resultant filtrate was subjected to molecular distillation at 235° C. The distillate thus obtained was washed with water and then deodorized at 235° C. for 1 hour to obtain Diglyceride Oil B.

Invention Products 1 to 3 and Comparative Products 1 to 3:

Diglyceride Oil A, Diglyceride Oil B, perilla oil (product of Ohota Yushi K.K.), rapeseed oil (product of Hohnen Co., Ltd.) were mixed at their corresponding weight ratios shown in Table 1. To the mixtures (each, 100 parts) were added vitamin E (MDE6000, product of Yashiro Co., Ltd.; 0.1 parts), silicone (KS-66, product of Shin-Etsu Chemical Co., Ltd.; 0.0002 parts) and citric acid (0.02 parts) to produce Invention Products 1 to 3 and Comparative Products 1 to 3. Analytic results of the oil compositions thus obtained are shown in Table 1.

Invention Product 4 and Comparative Product 4:

Diglyceride Oil B, rapeseed oil and perilla oil were mixed at their corresponding weight ratios shown in Table 3. To the mixtures (each, 100 parts) was added vitamin E (0.02 parts) to produce Invention Product 4 and Comparative Product 4. Analytic results of the oil compositions thus obtained are shown in Table 3.

Invention Product 5:

Diglyceride Oil B, rapeseed oil and linseed oil (product of Yoshihara Oil Mill, Ltd.) were mixed at its corresponding weight ratio shown in Table 3. To the mixture (100 parts) were added vitamin E (E Oil-600, product of Riken Vitamin Co., Ltd.; 0.2 parts), vitamin C palmitate (Vitamin C Palmitate, product of Roche Co.; 0.025 parts) and rosemary extract (Herbalox Type HT-O, product of Kalsec Co.; 0.025 parts) to produce Invention Product 5. Analytic results of the oil composition thus obtained are shown in Table 3.

TABLE 1

| | Invention product | | | Comparative product | | |
|---|---|---|---|---|---|---|
| | 1 | 2 | 3 | 1 | 2 | 3 |
| Rapeseed oil | 50 | 25 | 0 | 100 | 0 | 0 |
| Perilla oil | 25 | 25 | 25 | 0 | 0 | 100 |
| Diglyceride Oil A | 0 | 0 | 75 | 0 | 100 | 0 |
| Diglyceride Oil B | 25 | 50 | 0 | 0 | 0 | 0 |
| Composition of glycerides*[1] | | | | | | |
| TG | 78 | 56.2 | 34.8 | 99.2 | 13 | 98.6 |
| DG | 21.9 | 43.7 | 65.1 | 0.7 | 86.9 | 1.3 |
| 1,3-DG | 15.3 | 30.6 | 45.6 | 0.5 | 60.8 | 0.9 |
| 1,2-DG | 6.6 | 13.1 | 19.5 | 0.2 | 26.1 | 0.4 |
| MG | 0.1 | 0.1 | 0.1 | 0.1 | 0.1 | 0.1 |
| Composition of constitutive fatty acids*[2] Triglyceride | | | | | | |
| C16:0 | 5 | 5 | 8 | 5 | 12 | 85 |
| C18:0 | 2 | 2 | 3 | 2 | 4 | 3 |
| C18:1 (ω9) | 46 | 39 | 18 | 62 | 24 | 18 |
| C18:2 (ω6) | 19 | 20 | 25 | 19 | 51 | 25 |
| C18:3 (ω3) | 25 | 31 | 45 | 8 | 6 | 45 |
| Diglyceride | | | | | | |
| C16:0 | 3 | 3 | 12 | n.t. | 12 | 8 |
| C18:0 | 1 | 1 | 4 | n.t. | 4 | 3 |
| C18:1 (ω9) | 38 | 38 | 24 | n.t. | 24 | 18 |
| C18:2 (ω6) | 48 | 48 | 51 | n.t. | 51 | 25 |
| C18:3 (ω3) | 8 | 8 | 6 | n.t. | 6 | 45 | n.t.: Not tested.
*[1]Measured by gas chromatography after trimethylsilylation.
*[2]Measured by gas chromatography after methylation in accordance with the standard oils and fats analyzing test methods 2.4.1.2-1996 and 2.4.2.2-1996 (edited by the Japan Oil Chemists' Society).

Example 2

Repeated Test on Frying

Each of the oil compositions (Invention Products 1 to 3 and Comparative Products 1 to 3) prepared in Example 1 was used to repeatedly fry freezed vegetable croquettes. The acid value and coloring of each oil composition in the course of the frying, and the flavor of the cooked products were evaluated.

(Cooking Conditions)

Material of fry: Freezed vegetable croquettes (product of Ajinomono Co., Ltd.).

Amount of oil: 1500 g; No additional oil was supplied in the course of the frying.

Fryer: Electric fryer (NF-F150, manufactured by Matsushita Electric Industrial Co., Ltd.) was used.

(Flavor of Cooked Product)
- A: Far excellent because no unpleasant taste such as acid or astringent taste was observed;
- B: Excellent because an unpleasant taste was scarcely observed;
- C: An unpleasant taste such as acid or astringent taste was somewhat observed;
- D: Poor flavor because an unpleasant taste was observed.

TABLE 2

| | Properties of frying oil | | | | | | | | | | | |
|---|---|---|---|---|---|---|---|---|---|---|---|---|
| | Acid value | | | | | Color (10R + Y) | | | | | Flavor | |
| | After 2 hrs | After 4 hrs | After 6 hrs | After 8 hrs | After 10 hrs | After 2 hrs | After 4 hrs | After 6 hrs | After 8 hrs | After 10 hrs | Oil compn. | Cooked product |
| Invention Product 1 | 1.3 | 2.0 | 2.7 | 4.0 | 5.5 | 43 | 62 | 120 | 190 | 203 | A | A |
| Invention Product 2 | 1.3 | 2.1 | 2.8 | 4.1 | 5.6 | 44 | 64 | 139 | 254 | 271 | A | A |
| Invention Product 3 | 1.3 | 2.2 | 2.9 | 4.3 | 6.0 | 44 | 65 | 152 | 285 | 310 | B | B |
| Comparative product 1 | 1.3 | 2.1 | 2.8 | 4.0 | 5.4 | 42 | 60 | 79 | 101 | 182 | A | A |
| Comparative product 2 | 1.5 | 2.5 | 3.3 | 4.7 | 6.5 | 45 | 75 | 208 | 505 | 780 | C | C |
| Comparative product 3 | 1.5* | — | — | — | — | 74* | — | — | — | — | D* | D* |

*The evaluation as to the frying was stopped because odor became deteriorated remarkably at the stage after 2 hours from the beginning of the frying. Thus, only evaluation after 2 hours from the beginning of the frying was shown.

Oil temperature: 190° C.

Frying conditions:
A croquette (about 75 g) was fried over 5 minutes once every 15 minutes. After 2 minutes from the beginning of the frying, the croquette in the oil composition was turned from side to side. This frying operation was repeated 40 times (cumulative frying time: 10 hours).

(Acid Value of Oil Composition)

A part of the oil composition in the course of the frying was taken out every 2 hours to determine its acid value (Standard oils and fats analyzing test method 2.3.1-1996 (The Japan Oil Chemists' Society)). The value was expressed as a relative value that a value before the frying is regarded as 1.

(Coloring of Oil Composition)

A part of the oil composition in the course of the frying was taken out every 2 hours to measure its redness (R) and yellowness (Y) in accordance with the Lovibond method (Standard oils and fats analyzing test method 2.2.1.1-1996 (The Japan Oil Chemists' Society): instrument used; Lovibond PFX880 Tintometer, using 1-inch glass cell), thereby finding a calculated value (10R+Y) thereof.

In addition, the oil composition after 10 hours from the beginning of the frying and a cooked product fried at this time were evaluated by 10 panelists in accordance with the following evaluation standards.

(Flavor of Oil Composition)
- A: Far excellent because no unpleasant taste such as acid or astringent taste was observed;
- B: Excellent because an unpleasant taste was scarcely observed;
- C: An unpleasant taste such as acid or astringent taste was somewhat observed;
- D: Poor flavor because an unpleasant taste was observed.

All the oil compositions (Invention Products 1 to 3) according to the present invention scarcely underwent deterioration compared with the high diglyceride-containing oil (Comparative Product 2) and perilla oil (Comparative Product 3), and the flavor of the products cooked by using them was also good. In particular, the coloring of the oil compositions during the frying was markedly prevented. As described above, the oil compositions according to the present invention were good in flavor, hard to be colored and high in hydrolytic stability and the like even under severe conditions that heating was performed at a high temperature for a long period of time, and thus excellent in suitability for frying.

Example 3

Administration Test to Human (Test Sample)

Comparative Product 4 and Invention Product 4 prepared in Example 1 were used as test samples.

An oil-in-water type emulsified drink prepared so as to give an oil content of 10% was used upon ingestion of each test sample. The composition thereof is shown in Table 4. The drink obtained by using Invention Product 4 was good in flavor, appearance, emulsion stability, etc. The oil composition according to the present invention was able to be satisfactorily used in the application field of oil-in-water type emulsions.

TABLE 3

| | Invention Product 4 | Comparative Product 4 | Invention Product 5 |
|---|---|---|---|
| Rapeseed oil | 31.4 | 81.4 | 30 |
| Perilla oil | 18.6 | 18.6 | 0 |
| linseed oil | 0 | 0 | 20 |
| Diglyceride Oil B | 50 | 0 | 50 |
| Composition of glycerides*[1] | | | |
| TG | 56.2 | 99.3 | 55.9 |
| DG | 43.7 | 0.6 | 43.5 |
| 1,3-DG | 30.6 | 0.4 | 30.5 |
| 1,2-DG | 13.1 | 0.2 | 13.0 |
| MG | 0.1 | 0.1 | 0.6 |
| Composition of constitutive fatty acids*[2] | | | |
| Triglyceride | | | |
| C16:0 | 5 | 5 | 5 |
| C18:0 | 2 | 2 | 2 |
| C18:1 ($\omega$9) | 44 | 53 | 43 |
| C18:2 ($\omega$6) | 21 | 18 | 23 |
| C18:3 ($\omega$3) | 25 | 18 | 27 |
| Diglyceride | | | |
| C16:0 | 3 | n.t. | 3 |
| C18:0 | 1 | n.t. | 1 |
| C18:1 ($\omega$9) | 38 | n.t. | 39 |
| C18:2 ($\omega$6) | 48 | n.t. | 47 |
| C18:3 ($\omega$3) | 8 | n.t. | 9 | n.t.: Not tested.
*[1]Measured by gas chromatography after trimethylsilylation.
*[2]Measured by gas chromatography after methylation according to the same methods described in Table 1.

TABLE 4

Formulation of test drink

| | % |
|---|---|
| Oil | 10 |
| Water | 47.8 |
| Seasoning TORYS CONC (product of Suntory Limited) | 25 |
| Reducing starch hydrolyzate PO-300 (product of Towa Chemical Industry, Co., Ltd.) | 6.44 |
| Reducing starch hydrolyzate PO-500 (product of Towa Chemical Industry, Co., Ltd.) | 6.44 |
| Erythritol | 3.32 |
| Emulsifier Polyglycerol SY Glyster MS-500 (product of Sakamoto Yakuhin Kogyo Co., Ltd.) | 1 |

The above materials other than the oil were mixed and heated to 60° C. into a solution. The oil heated to 60° C. was added to the solution and emulsified by means of T.K. homomixer (product of TOKUSHU KIKA KOGYO CO., LTD.) at 6000 rpm. The emulsion was then treated by homogenizer (product of SANWA MACHINE CO., INC.) at 200 Kgf/cm$^2$ (2 pass) to prepare an emulsified drink.

(Subject and Testing Method)

This test was performed with sufficient consideration according to the sprit of Helsinki Declaration. The subjects were 16 healthy men aged 27 to 44 years. The ingestion time, contents and amount of a supper in the day before the test were unified as to all the subjects. Ingestion of other foods and drinks than water was forbidden from the ingestion of the supper to the beginning of the test at the day after the supper.

In the test, the test drink was ingested in an amount sufficient to give a lipid of 10 g per 60 kg of body weight to collect blood before the ingestion and after 3, 4 and 5 hours from the ingestion. The test prescribed that the subjects keep quiet during the test, and ingestion of other foods and drinks than water are forbidden.

An crossover test was carried out as to the 2 test samples in accordance with the above-described method.

(Analysis of Blood)

The blood samples collected were used to evaluate the behavior of serum lipids after the ingestion of the test samples. More specifically, serum neutral lipid after the ingestion of each test sample and chylomicron TG that is a lipoprotein lipid formed in the blood from lipids absorbed through a small intestine were determined.

The value of the serum neutral lipid after the ingestion of the test sample is shown in Table 5 as a rate of change (%) of the serum neutral lipid value regarding a value before the ingestion of the lipid as 100. A significance test was conducted by the paired-t test. As a result, the invention product was found to have an effect of significantly inhibiting the increase of serum neutral lipid after 3 hours from the ingestion of the test sample compared with the comparative product (level of significance p<0.05).

TABLE 5

Rate (%) of change of serum neutral lipid value after ingestion of test sample

| | Before ingestion | After 3 hours | After 4 hours | After 5 hours |
|---|---|---|---|---|
| Comparative Product 4 | 100 | 156 ± 7 | 136 ± 7 | 109 ± 5 |
| Invention Product 4 | 100 | 139 ± 7* | 132 ± 5 | 119 ± 3 |

Mean ± standard error
*Significance p < 0.05

The results as to chylomicron TG after the ingestion of the test samples are shown in Table 6. The paired-t test was performed likewise. As a result, the invention product was found to have an effect of significantly inhibiting the increase of chylomicron TG after 3 hours from the ingestion of the test sample (level of significance p<0.05).

TABLE 6

Chylomicron TG (mg/dl) after ingestion of test sample

| | Before ingestion | After 3 hours | After 4 hours |
|---|---|---|---|
| Comparative Product 4 | 3 ± 1 | 21 ± 4 | 11 ± 3 |
| Invention Product 4 | 3 ± 1 | 15 ± 2* | 10 ± 2 |

Mean ± standard error
*Significance p < 0.05

The oil composition (Invention Product 4) according to the present invention inhibited the increase of chylomicron TG formed from lipids absorbed through a small intestine, thereby significantly inhibiting the increase of serum neutral lipid after eating.

Example 4

Soft Capsule

DHA 22 (product of MARUHA CORP.; 40 parts by weight), corn oil (10 parts by weight), catechin (0.2 parts by weight) and tocopherol (0.05 parts by weight) were mixed with Diglyceride Oil A (50 parts by weight) described in Example 1 to prepare an oil composition (Invention Product 6). This composition (300 mg) was encapsulated into a soft capsule body in an oval form to formulate a soft capsule preparation.

Example 5

Frizzled Bean Sprouts

The oil composition (Invention Product 3; 8 parts by weight) prepared in Example 1 was placed on a frying pan (24 cm), and the frying pan was heated by a gas heater. After 30 seconds, bean sprouts (200 parts by weight) were placed on the frying pan and frizzled for 30 seconds. Common salt (1.4 parts by weight) was then added, and the bean sprouts were further frizzled for 30 seconds to cook frizzled bean sprouts. The frizzled bean sprouts thus obtained were good in all of flavor, appearance and operability upon cooking. The oil composition according to the present invention was able to be satisfactorily used in the application field of frizzled foods.

Example 6

Chinese Dressing (Separation Type)

|  | (parts by weight) |
| --- | --- |
| Oil composition (Invention Product 1) | 25 |
| Sesame oil | 5 |
| Soy sauce | 25 |
| Vinegar (acid content: 10%) | 11 |
| Japanese wine | 6 |
| Refined sucrose | 3 |
| Common salt | 1.4 |
| Oyster sauce | 0.2 |
| Sodium glutamate | 0.15 |
| Chinese bouillon (powder) | 0.1 |
| Garlic oil | 0.02 |
| Ginger oil | 0.01 |
| Water | 23.12 |

After the components other than the oil composition and sesame oil were mixed with one another, the oil composition and sesame oil were added to prepare a Chinese dressing (separation type). The Chinese dressing (separation type) thus obtained was good in both flavor and appearance. The oil composition according to the present invention was able to be satisfactorily used in the application field of dressings.

Example 7

Short Bread

|  | (parts by weight) |
| --- | --- |
| Oil composition (Invention Product 4) | 200 |
| Weak flour | 350 |
| Strong flour | 150 |
| Refined sucrose | 150 |
| Whole egg | 125 |
| Common salt | 2.5 |

Refined sucrose and common salt were placed in a bowl and stirred by a Hobart mixer. The whole egg was gradually added to the mixture, and stirring was conducted again by the Hobort mixer. A mixture of weak flour and strong flour prepared in advance was added in 3 portions, and the resultant mixture was further stirred by the Hobart mixer. A dough thus prepared was divided into small portions (each, 25 g), and each portion was put into a metal frame. The portion was baked in an oven (160° C., 50 minutes), removed from the frame and allowed to cool down to prepare short breads. The short breads thus obtained were good in both flavor and appearance. The oil composition according to the present invention was able to be satisfactorily used in the application field of bakery foods.

Example 8

Margarine-Like Spread

| (Oil phase) | |
| --- | --- |
|  | (parts by weight) |
| Oil composition (Invention Product 2) | 33.38 |
| Hardened palm oil (IV = 2) | 4 |
| Hardened soybean oil (IV = 43) | 2 |
| Monoglyceride | 0.5 |
| Lecithin | 0.5 |
| Polyglycerol condensed ricinolic acid ester | 0.5 |
| Flavor | 0.1 |
| Vitamin E | 0.02 |

| (Water phase) | |
| --- | --- |
|  | (parts by weight) |
| Distilled water | 57.4 |
| Nonfat dry milk | 0.3 |
| Common salt | 1.3 |

The above oil phase and water phase were separately prepared and then mixed and emulsified by a homomixer. The emulsion thus obtained was quenched and plasticized by a method known per se in the art, thereby preparing a margarine-like spread. The margarine-like spread thus obtained was good in all of flavor, appearance and emulsion stability. The oil composition according to the present invention was able to be satisfactorily used in the application field of water-in-oil type emulsions.

Example 9

Oxidation Stability Test

Invention Product 5 prepared in Example 1 was used as a sample to evaluate it as to oxidation stability in accordance with the standard oils and fats analyzing test method 2.5.1.2-1996 (edited by The Japan Oil Chemists' Society). As a result, the Rancimat induction time of Invention Product 5 was 4.6 hours, and it was hence found that the oil composition has good oxidation stability.

Example 10

Fried Food (Tempura)

Invention Product 5 prepared in Example 1 was used to cook tempura under the following conditions.

Amount of oil: 600 g (Chinese pan).
Oil temperature: 180° C., heated (medium fire) by a gas heater.
Material:
- eight prawns (black tiger),
- eight pieces of lotus root
- eight pieces of pumpkin
- eight pieces of pimento (cut into halves) and eight pieces of eggplant (cut into halves).

Coating of tempura:
- wheat flour (100 g)
- egg (50 g) and
- water (150 g).

The tempura thus obtained was good in both flavor and appearance. The oil composition after the cooking of tempura was also good likewise. The oil composition according to the present invention was able to be satisfactorily used in the application field of fried foods.

Example 11

Emulsion Stability Test

The oil compositions (Invention Product 1, Comparative Product 1 and Comparative Product 2) prepared in Example 1 were used to prepare oil-in-water type emulsified drinks in accordance with their corresponding formulations shown in Table 4. The emulsified drinks thus obtained were respectively charged into 50-ml glass-made sampling bottles and hermetically sealed. After the bottles were left at rest at 20° C. for a week, the emulsified state of each drink was visually observed. The results thereof are shown in Table 7.

TABLE 7

| Oil composition | Right after emulsification | After 1 week at 20° C. |
|---|---|---|
| Invention Product 1 | A | A |
| Comparative Product 1 | A | A |
| Comparative Product 2 | A | D |

A: Emulsion was very stable because neither oil off nor separation of water was observed;
B: Emulsion was stable because oil off and separation of water were scarcely observed;
C: Emulsion was somewhat unstable because oil off and separation of water were observed;
D: Emulsion was unstable because separation occurred.

It was found that the emulsified drink using Invention Product 1 has good emulsion stability.

Example 12

Animal Test

Feed B (comparative) obtained by adding triglyceride (TAG; 6%) to a composition based on a high-fat and high-sucrose feed shown in Table 8 was given to a control group, and Feed C (comparative) obtained by adding diglyceride (DAG; 6%) in place of TAG (6%) or Feed A (invention) obtained by adding DAG (3%) and linseed oil (3%) was given to a test group and freely ingested (in each group, n=10). Changes of increase in body weight and increase in body weight per calorie after breeding for 8 weeks are shown in Table 9.

TABLE 8

| Component of feed (wt. %) | Feed A (invention) | Feed B (comparative) | Feed C (comparative) |
|---|---|---|---|
| linseed oil*1 | 3 | 0 | 0 |
| DAG*2 | 3 | 0 | 6 |
| TAG*3 | 0 | 6 | 0 |
| Fat*4 | 24 | 24 | 24 |
| Sucrose | 13 | 13 | 13 |
| Casein | 20 | 20 | 20 |
| Cellulose | 4 | 4 | 4 |
| Mineral mixture*5 | 3.5 | 3.5 | 3.5 |
| Vitamin mixture*6 | 1 | 1 | 1 |
| Potato starch | 28.5 | 28.5 | 28.5 |

*1 Product of Yoshihara Oil Mill, Ltd.
*2 Diglyceride Oil B.
*3 Safflower oil (product of Nisshin Oil Mills, Ltd.; 46.4% by weight) + Rapeseed oil (product of Nisshin Oil Mills, Ltd.; 49.1% by weight) + perilla oil (product of Ohota Yushi K. K.; 4.5% by weight).
*4 Lard (5% by weight) + TAG (19% by weight).
*5 AIN-76 prescription
*6 AIN-76 prescription + choline bitartrate (20 g/100 g)

TABLE 9

| | Body weight | | | |
|---|---|---|---|---|
| Feed | Initial (g) | After 8 weeks (g) | Increase in body weight (g) | Increase in body weight (g/cal) |
| A (invention) | 23.4 ± 1.1 | 31.3 ± 2.2 | 8.0 ± 2.0 | 10.1 ± 2.5 |
| B (comparative) | 23.4 ± 0.8 | 33.4 ± 3.1 | 10.0 ± 3.0 | 12.3 ± 3.8 |
| C (comparative) | 23.4 ± 1.4 | 32.3 ± 1.6 | 8.9 ± 1.6 | 11.5 ± 2.1 |

It was clearly known that when Feed A according to the present invention was ingested, increase in body weight and increase in body weight per calorie are inhibited. The oil composition according to the present invention was able to be satisfactorily used in the application field of feeds.

As described above, the oil compositions according to the present invention are mixed oils composed of triglycerides containing a great amount of ω3 type unsaturated fatty acids among constitutive fatty acids in glycerides and diglycerides containing a small amount of the ω3 type unsaturated fatty acids and thus are good in flavor, hard to be colored, excellent in hydrolysis stability and resistance to oxidation, good in emulsion stability and excellent in intake balance among fatty acids even under severe conditions that heating is performed at a high temperature for a long period of time, can be widely developed to medicinal preparations and foods and moreover exhibit an excellent inhibitory effect on accumulation of body fat by ingestion of a small amount of diglycerides.

The invention claimed is:

1. An oil composition comprising the following components (A) and (B): (A) 15 to 70% by weight of diglycerides in which less than 15% by weight of the constitutive fatty acids are ω3 type unsaturated fatty acids; and (B) 30 to 85% by weight of a triglyceride in which at least 15% by weight of the constitutive fatty acids are ω3 type unsaturated fatty acids.

2. The oil composition according to claim 1, wherein among the ω3 type unsaturated fatty acids in the component (B), α-linolenic acid is contained in an amount of at least 50% by weight.

3. The oil composition according to claim 1 or 2, which further comprises 0.004 to 5% by weight of an antioxidant.

4. The oil composition according to any one of claims 1 to 2 which further comprises 0.02 to 0.5% by weight of a crystallization inhibitor.

5. The oil composition according to any one of claims 1 to 2, which further comprises at least 0.05% by weight of a phytosterol.

6. A food comprising the oil composition according to any one of claims 1 to 2.

7. The food according to claim 6, wherein said food is an oil-in-water type oil-containing food.

8. The food according to claim 6, wherein said food is a water-in-oil type oil-containing food.

9. The food according to claim 6, wherein said food is a portable oil-containing food.

10. The food according to claim 6, wherein said food is a bakery food.

11. A feed comprising the oil composition according to any one of claims 1 to 2.

12. A pharmaceutical comprising the oil composition according to any one of claims 1 to 2.

13. A cooking oil comprising the oil composition according to any one of claims 1 to 2.

* * * * *